United States Patent [19]

Hock

[11] Patent Number: 5,362,857
[45] Date of Patent: Nov. 8, 1994

[54] PURIFICATION OF PLASMINOGEN ACTIVATOR INHIBITOR 2 BY IMMUNOAFFINITY CHROMATOGRAPHY

[75] Inventor: Johann Hock, Marburg, Germany

[73] Assignee: Behringwerke Aktiengesellschaft, Marburg, Germany

[21] Appl. No.: 56,393

[22] Filed: May 4, 1993

[30] Foreign Application Priority Data

May 6, 1992 [DE] Germany .............................. 4214999

[51] Int. Cl.$^5$ ..................... C07K 3/20; C07K 15/06
[52] U.S. Cl. ................................... 530/395; 530/413
[58] Field of Search ............................. 530/395, 413

[56] References Cited

U.S. PATENT DOCUMENTS

| 5,134,065 | 7/1992 | Sanzo et al. | 435/703 |
| 5,204,256 | 4/1993 | Radtke et al. | 435/226 |

FOREIGN PATENT DOCUMENTS

| 0418647A1 | 3/1991 | European Pat. Off. |
| 3713272A1 | 11/1988 | Germany. |
| WO91/09124 | 6/1991 | WIPO. |

OTHER PUBLICATIONS

Astedt, B., et al., "Purification of a Specific Placental Plasminogen Activator Inhibitor by Monoclonal Antibody and Its Complex Formation with Plasminogen Activator," Medline Abstract No. 85193106 (1985).

Radtke, K. P., et al., "Isolation of Plasminogen Activator Inhibitor-2 (PAI-2) from Human Placenta," Medline Abstract No. 91214546 (1990).

Astedt, B., et al., "Purification of a Specific Placental Plasminogen Activator Inhibitor by Monoclonal Antibody and Its Complex Formation with Plasminogen Activator," Thrombosis and Haemostasis: 122–125 (F. K. Schattauer Verlag GmbH, 1985).

Abstract of German Patent Application No. DE 3722673, entitled: "New DNA Encoding Complete Plasminogen Activator Inhibitor Type 2-Expressed Protein and Derived Antibodies, Useful Therapeutically and Diagnostically".

"Purification of a Specific Placental Plasminogen Activator Inhibitor by Monoclonal Antibody and Its Complex Formation with Plasminogen Activator", Astedt et al., Thrombosis and Haemostasis, 53:122–125 (1985).

"Continuous cultures of fused cells secreting antibody of predefined specificity", Koehler et al., Nature, 256:495–497 (1985).

"Antibody Production by Hybridomas", Goding, J. W., Journal of Immunological Methods, 39:285–308 (1980).

"Isolation of Plasminogen Activator Inhibitor-2 (PAI-2) from Human Placenta", Radtke et al., Biol. Chem. Hoppe-Seyler, 371:1119–1127 (1990).

"Cloning and expression of a cDNA coding for a human monocyte-derived plasminogen activator inhibitor", Antalis et al., *Proc. Natl. Acad. Sci. USA*, 85:985–989 (1988).

"Plasmid Vectors Carrying the Replication Origin of Filamentous Single-Stranded Phages", Cesareni et al., Genetic Engineering, 9:135–154 (1987).

"Expression of the human blood coagulation protein Factor XIIIa in *Saccharomyces cerevisiae*: dependence of the expression levels from host-vector systems and medium conditions", Broeker et al., Applied Microbiology and Biotechnology, 34:756–764 (1991).

Wun et al., "An Inhibitor of Plasminogen Activator . . . ", Jour. of Biol. Chem., vol. 262, No. 6, 1987 pp. 3646–3653.

Harris, E. L. V. et al., "Protein Purification Methods", IRL Press, 1989, pp. 255–257.

*Primary Examiner*—Michael G. Wityshyn
*Assistant Examiner*—C. Sayala
*Attorney, Agent, or Firm*—Finnegan, Henderson, Farabow, Garrett & Dunner

[57] ABSTRACT

The invention relates to a process for the purification by immunoaffinity chromatography of plasminogen activator inhibitor 2 (PAI-2) and to monoclonal antibodies which are suitable for a process of this type.

4 Claims, No Drawings

PURIFICATION OF PLASMINOGEN ACTIVATOR INHIBITOR 2 BY IMMUNOAFFINITY CHROMATOGRAPHY

The invention relates to a process for the purification of plasminogen activator inhibitor 2 (PAI-2) by immunoaffinity chromatography and to monoclonal antibodies which are suitable for this purpose.

Plasmin is a central protease for many physiological processes such as, fibrinolysis, cell migration, cell differentiation or remodelling tissue. Plasmin activity is regulated inter alia via the proteolytic conversion of the proenzyme plasminogen into the active protease plasmin by the plasminogen activators tPA (tissue type plasminogen activator) and urokinase. The activity of these proteases is in turn controlled by specific inhibitors such as PAI-1 or PAI-2.

PAI-2 is found, inter alia, in human placental tissue, in plasma from pregnant women and in monocytes. PAI-2 is isolated from placenta as a non-glycosylated protein and appears in SDS polyacrylamide gel electrophoresis as a double band with molecular weights of 45,000 and 51,000 dalton respectively. The 51,000 dalton form can be converted into the 45,000 dalton form by reduction of disulfide bridges. The 51,000 dalton form is thus an oxidation product of the 45,000 dalton form. Part of the PAI-2 is present in the placenta in the form of complexes with other proteins, for example vitronectin. SDS Polyacrylamide gel electrophoresis of purified preparations also reveals PAI-2 oligomers which can be convened under reducing conditions into the monomeric form. PAI-2 is isolated as glycosylated protein with a molecular weight of about 65,000 dalton from plasma from pregnant women, whereas both the glycosylated and the non-glycosylated form can be isolated from monocyte cultures. All the PAI-2 forms described are able to inhibit urokinase. The meaning of PAI-2 hereinafter includes all forms with inhibitory activity (non-glycosylated, glycosylated, oligomers and complexes with other proteins).

High purity of proteins from human tissues or body fluids for therapeutic purposes, entails a lower risk of virus transmission. Purification of recombinant human proteins from microorganism cultures for therapeutic purposes must result in a very high purity of these proteins in order to ensure removal as completely as possible of antigenic host cell proteins. Affinity chromatography with monoclonal antibodies is a method which allows to achieve an extremely high purity. Since purification even of complex protein mixtures by means of immunoaffinity chromatography requires only a few purification steps, a higher yield than in conventional processes can also be achieved.

Purification of PAI-2 by immunoaffinity chromatography has already been described (Astedt, B. et al. (1985) Thromb. Haemost. 53:122-125). However, the elution conditions used, namely 2 mol/l KSCN, 0.01% Triton, result in at least partial denaturation of PAI-2. The described process is thus unsuitable for obtaining native PAI-2 for example for therapeutic purposes.

The object of the invention is therefore to develop a process for the purification of native PAI-2 by immunoaffinity chromatography from starting materials such as placenta, monocytes or extracts or culture supernatants of recombinant cells which contain the genetic information for PAI-2.

It has been found, surprisingly, that it is possible for PAI-2 to be bound to immobilized monoclonal antibodies and to be eluted in active form by aqueous solutions of low ionic strength or with distilled water.

The invention relates to a process for the purification of native PAI-2 by immunoaffinity chromatography, which comprises contacting a solution which contains PAI-2 with a monoclonal antibody against PAI-2 which is bound to an insoluble support material, separating affinity material and liquid from one another, and eluting PAI-2 from the affinity material in biologically active form.

The invention also relates to monoclonal antibodies against PAI-2 which are suitable for the purification of native PAI-2 by immunoaffinity chromatography. It is characteristic of such antibodies that PAI-2 is specifically bound to them and can be dissociated again under mild conditions, which do not impair its biological activity. Monoclonal antibodies for the purpose of the invention are also the immunoreactive fragments of monoclonal antibodies, which are known per se to the person skilled in the art, such as, for example, F(ab')2, Fab or Fv fragments and antigen-binding Single chains of antibody molecules.

Suitable monoclonal antibodies can be prepared by the method of Köhler and Milstein (Nature 256:285-308) or one of the many variants of their method (for example Goding, J. W. (1980), J. Immunol. Meth. 39:285-308), which are known per se to the person skilled in the art, for example in the following way:

Mammals, preferably mice or rats, are immunized by several injections at intervals each of 1-4 weeks with a liquid containing PAI-2, preferably an emulsion of purified PAI-2 in Freund's adjuvant. To prepare for cell fusion, PAI-2 is administered, preferably intraperitoneally or intravenously, in aqueous solution 3-5 days before the planned date of cell fusion.

To obtain antibody-producing cells, an immunized animal is sacrificed, a lymphatic organ, preferably the spleen, is removed, and the lymphocytes are isolated. In order to obtain antibody-producing cells which grow permanently in cell culture, the lymphocytes must be immortalized. This can be done in a variety of ways, for example by transformation with Epstein-Barr virus or retroviruses. However, the lymphocytes are preferably fused with myeloma cells. Particularly suitable myeloma cell lines are those from BALB/c mice which secrete no immunoglobulins, for example the cell lines SP2/0-Ag14 or X63-Ag8.653. The cells can be fused by incubation with polyethylene glycol with a molecular weight of 1000-6000 in 30-60% strength solution, but other processes, for example electrofusion, are also suitable. Hybrids of lymphocytes and myeloma cells (hybridomas) are selected and multiplied by cultivation in a suitable nutrient medium. The hybridomas are tested for the production of specific antibodies 1-3 weeks after the cell fusion. A large number of test systems which are known to the person skilled in the art are available for this. An ELISA test system in which PAI-2 is adsorbed on to a solid phase is preferably used. The hybridoma cell supernatants are initially contacted with PAI-2, and PAI-2-specific antibodies are detected by incubation with an enzyme-labeled antibody against mouse IgG and subsequent addition of a chromogenic substrate for the labeling enzyme. Cells which produce specific antibodies against PAI-2 are cloned by plating out with microscopic inspection or by the limiting dilution method. Clonal cells lines are multiplied for obtaining antibodies in vitro. Monoclonal antibodies can be obtained from the culture medium. A large number of processes are available for this, and affinity chromatography on immobilized protein A or PAI-2 is preferably carried out.

The purified monoclonal antibodies are then tested for their suitability for immunoaffinity chromatography. To do this, antibodies are coupled to a suitable insoluble support material by processes familiar to the person skilled in the art. Supports used in affinity chromatography comprise a variety of materials, for example derivatives of agarose, polyacrylamide or cellulose. The antibodies can be coupled after activation of the support, for example with cyanogen bromide or carbodiimide. Various other support materials and coupling methods are known to the person skilled in the art. Suitable in principle as support is every customary material and every coupling method in which the activity of the coupled antibody not significantly altered. The affinity gels are then tested for their suitability for the purification of PAI-2. To do this, a PAI-2-containing solution is pumped over the affinity gel, and the PAI-2 activity in the flow-through is determined. Gels on to which PAI-2 is absorbed are suitable for the immunoaffinity chromatography.

In a preferred procedure, the binding of PAI-2 to the immunoaffinity gel takes place from a solution with a conductivity of $\geq 5$ mS at a pH between 5.5 and 8.5 and at a temperature from $+4°$ C. to $+37°$ C. The buffer particularly preferably contains 0.05 mol/l phosphate or tris and 0–3.0 mol/l NaCl.

The critical step is the elution of PAI-2 from the affinity gel. The dissociation of the antigen-antibody complex frequently requires conditions under which there is irreversible destruction of PAI-2 activity. It is therefore necessary to find mild elution conditions which permit dissociation of the antigen-antibody complex with retention of PAI-2 activity. It is possible in principle to use a variety of eluents for this, for example organic solvents, detergents, solutions of very low or very high ionic strength or combinations of various eluents. These and other elution methods (for example temperature-dependent) are known to the person skilled in the art. Preferably used for the elution of PAI-2 are solutions of very low ionic strength (conductivity$\leq 3$ mS) at a pH between 5.5 and 8.5, particularly preferably distilled water. It is possible to add various substances to the eluent, for example sugars, sugar alcohols, polysaccharides, amino acids or proteins, in order to stabilize the eluted PAI-2.

The following examples illustrate the invention:

EXAMPLE 1

Preparation and selection of monoclonal antibodies a) Immunization of mice

Female BALB/c mice were immunized by subcutaneous injection of an emulsion of 50 μg of PAI-2 (prepared as described by Radtke et al. (1990) Biol. Chem. Hoppe-Seyler, 371:1119–1127) in complete Freund's adjuvant (day 1 ). On each of days 28 and 56, 30 μg of PAI-2 emulsified in incomplete Freund's adjuvant were likewise injected subcutaneously. This was followed on day 92 by an intraperitoneal injection of 100 μg of PAI-2 in 0.5 ml of physiological saline.

b) Fusion of lymphocytes with myeloma cells

On day 95, after removal of the spleen, lymphocytes were obtained by mechanical disintegration (about $1 \times 10^8$ cells). The lymphocytes were washed in Dulbecco's modified Eagle's medium (DMEM), mixed with $5 \times 10^7$ cells of the myeloma cell line SP2/0-Ag14 and spun down. After complete removal of the supernatant, 0.5 ml of a 50% strength solution of polyethylene glycol 4000 in DMEM was added dropwise to the cell pellet over the course of one minute.

The suspension was incubated at 37° C. for 90 seconds and then diluted by addition of 7.5 ml of DMEM over a period of 5 minutes. After incubation at room temperature for 10 minutes, the volume was made up to 40 ml with DMEM, and the cells were spun down. The supernatant was removed by aspiration and then the cells were resuspended in DMEM with 20% fetal calf serum (FCS) and 13.6 mg/ml hypoxanthine, 0.18 mg/ml aminopterin, 3.9 mg/ml thymidine (HAT medium) and inoculated on 6 microtiter plates (200 μl per well). Medium was rexchanged at intervals of 3–4 days, and HAT medium was replaced by HT medium after 10 days.

c) Test for antibodies against PAI-2

14 Days after the fusion, the culture supernatants of the cells were tested for antibodies against PAI-2 by enzyme immunoassay: polystyrene microtest plates were incubated with 0.1 μg/ml PAI-2 in 0.1 mol/l NaCl, 0.1 mol/l sodium acetate, pH 5.5 (4° C., 24 h). Subsequently, cell culture supernatants were applied (37° C., 2 h) followed by incubation with a peroxidase-conjugated antibody against mouse IgG. The substrate used was a solution of 0.1% (weight/volume) 2,2'-azinodi(3-ethylbenzothiazoline-6-sulfonate) and 0.012% (volume/volume) $H_2O_2$ in 0.1 mol/l citric acid, 0.1 mol/l in $Na_2HPO_4$, pH 4.5. Incubation at 37° C. for 30 min was followed by measurement of the absorption at 405 nm. Between the individual incubation steps, the wells of the assay plates were washed with PBS/$^R$Tween.

d) Cloning of antibody-producing cell lines

Cells whose supernatants showed a strongly positive reaction (absorption>1.5) in the enzyme immunoassay described were cloned by the limiting dilution method. For this, about 60 cells containing DMEM with 20% FCS and 5% human endothelial culture supernatant (from Costar) were distributed over the 96 wells of a cell culture plate. Single clones were identified under the microscope and tested for antibody production. The cloning was repeated twice.

e) Purification of monoclonal antibodies

For production of antibodies, clonal cell lines were transferred into roller bottles and cultivated in Iscove's modified Dulbecco's medium. Cells were removed by centrifugation and filtration through paper filters and were concentrated about 10-fold by ultrafiltration. The concentrate was passed through protein A-$^R$Sepharose CL-4B, and bound IgG was eluted with 0.2 mol/l glycine/HCl, pH 3.0. The protein-containing fractions were dialyzed against 0.1 mol/l citrate, pH 6.5, and concentrated to about 5 mg/ml by ultrafiltration.

f) Selection of antibodies for immunoaffinity chromatography

Monoclonal antibodies suitable for the immunoaffinity chromatography were selected by a modified sandwich ELISA. Three microtest plates were coated with monoclonal antibodies against PAI-2 (5 μg/ml in 0.1 mol/l NaCl, 0.1 mol/l sodium acetate, pH 5.5) by incubation for 24 h at +4° C. Subsequently 1 μg/ml PAI-2 in PBS/$^R$Tween with 2% bovine serum albumin was added to the coated wells and incubated for 2 h at 37° C. After that each plate was submitted to an individual washing procedure (incubation with washing solution for 15 min with exchange of solution after each 5 min). Washing solutions were PBS, 3 mol/l NaSCN, or distilled water. The plates were then incubated (37° C., 2 h) with a peroxidase-conjugated polyclonal antibody against PAI-2. The following steps (washing, substrate incubation, measurement) were carried out as described in Example 1c. Plates washed with PBS served as positive control for the binding of PAI-2 to the monoclonal antibodies, while plates washed with NaSCN served as positive control for the elution of PAI-2 from the monoclonal antibodies. Monoclonal antibodies which had bound PAI-2 in the PBS control ($A_{405}>1.5$) and showed no reaction after washing with distilled water ($A_{405}<0.5$), were used to produce affinity gels.

g) Production of affinity gels

Monoclonal antibodies which had been purified as in Example 1e and selected as in 1f were coupled in the following way to $^R$Sepharose 4B which had been activated with cyanogen bromide: 1.5 g of RSepharose 4B activated with cyanogen bromide were suspended in 1 mmol/l HCl, packed into a chromatography column and washed with 300 ml of HCl (1 mmol/l). The column was then equilibrated with 10 ml of coupling buffer (0.1 mol/l trisodium citrate, pH 6.5), and the gel was transferred into a closable vessel with 4 ml of an antibody solution (5 mg/ml in coupling buffer) and shaken at 23° C. for 2 hours. The gel was then again placed in the column, washed with 50 ml of coupling buffer, placed in a closable vessel with 20 ml of ethanolamine HCl (1 mol/l, pH 8.0) and shaken at 23° C. for two hours. The gel was again transferred into the column and washed successively with 100 ml each of 0.1 mol/l sodium acetate, 1 mol/l NaCl, pH 4.0 and 0.1M tris, 1M NaCl, pH 8.0. The process was repeated 5 times. Finally, the gel was equilibrated with PBS and was ready for use.

EXAMPLE 2

Purification of PAI-2 from a monocyte cell line by immunoaffinity chromatography The cell line U-937 (ATCC CRL 1593) was cultivated in DMEM with 10% FCS in cell culture bottles (650 cm$^2$). When a cell density of $1-2\times 10^6$/ml was reached, the cells were washed twice with serum-free DMEM and again inoculated in the same medium into cell culture bottles. 30 ng/ml 12-myristoyl-13-acetyl-phorbol were added and the cells were incubated for a further 72 h. 21 of cell supernatant were obtained by clarifying filtration and concentrated about 40-fold by ultrafiltration. The resulting concentrate was pumped over an affinity gel with a monoclonal antibody (as in Example 1 g). Subsequently, unbound protein was washed off the column with 100 ml of washing buffer (1.0 mol/l NaCl, 0.02 mol/l Na$_2$HPO$_4$, pH 7.4). PAI-2 was then eluted with distilled water. The eluate was dialyzed against 0.15 mol/l NaCl, 0.02 mol/l glycine, pH 7.2, and pumped over ConA-$^R$Sepharose. After the ConA-$^R$Sepharose had been washed with 0.15 mol/l NaCl, 0.02 mol/l glycine, pH 7.2, elution was carried out with 0.5 mol/l methyl α-D-mannopyranoside m the same buffer. Flow-through and eluate from the ConA-$^R$Sepharose were subjected to SDS polyacrylamide gel electrophoresis under reducing conditions. The unbound fraction appeared as a band with 45,000 dalton and corresponded to the non-glycosylated form of PAI-2. The specific activity was 170,000 U/mg. The eluate likewise appeared as a single band with a molecular weight of 65,000 dalton and corresponded to glycosylated PAI-2. The specific activity was 110,000 U/mg. One unit of PAI-2 is defined as the amount which inhibits one international unit of urokinase.

EXAMPLE 3

Purification of PAI-2 from recombinant yeast cells by immunoaffinity chromatography The PAI-2-specific cDNA which is described by Antalis et al. (Proc. Natl. Acad. Sci. U.S.A. 85,985-989 (1988)) was cloned into the yeast/E. coli shuttle vector pEMBLyex4 (Cesareni and Marry, in: Genetic Engineering, Vol. 9, 135-154, J. K. Setlow, ed., Plenum Press, 1987) in such a way that the expression of PAI-2 is under the control of the regulatable GAL/CYC hybrid promoter. The new recombinant plasmid pPAI-2-A-10 was transformed into Saccharomyces cerevisiae, strain CL3AB YS86 and transformed yeast cells were selected on selective medium. The molecular biological and microbiological techniques used are described by Bröker et al. (Appl. Microbiol. Biotechnol. 34, 756-764 (1991)). S. cerevisiae CL3ABYS86 [pPAI-2-A-10] transformants were grown in shake cultures and, after incubation for four days, the cells were disrupted in a glass bead mill. After centrifugation of the lysate and sterilization by filtration it was possible in a urokinase inhibition assay to detect in the supernatant PAI-2 in a concentration of about 45 mg/l culture broth. 50 ml of a lysate obtained in this way were pumped over an affinity gel with a monoclonal antibody (as in Example 1 g). Subsequently unbound protein was washed off the column with 100 ml of washing buffer (1.0 mol/l NaCl, 0.02 mol/l Na$_2$HPO$_4$, pH 7.4). PAI-2 was then eluted with distilled water. The specific activity was 140,000-160,000 U/mg; the protein appeared in SDS polyacrylamide gel electrophoresis under reducing conditions as one band with a molecular weight of 45,000 dalton.

I claim:

1. A process for obtaining pure plasminogen activator inhibitor 2 (PAI-2) in biologically active form by immunoaffinity chromatography, which comprises contacting a solution which contains PAI-2 with a monoclonal antibody against PAI-2 which is bound to an affinity support material, separating affinity material and liquid from one another, and eluting PAI-2 from the affinity material in biologically active form and having a specific activity of 110,000 to 170,000 U/mg.

2. The process as claimed in claim 1, wherein an immunoreactive F(ab')$_2$, Fab, or Fv fragment of a monoclonal antibody is bound to the support material.

3. The process as claimed in claim 1, wherein elution is carried out with a buffer with a conductivity <3 mS at a pH of 5.5-8.5 or with distilled water.

4. The process as claimed in claim 1, wherein an antigen-binding single chain of a monoclonal antibody is bound to the support material.

* * * * *